(12) United States Patent
Amelia et al.

(10) Patent No.: US 8,223,920 B2
(45) Date of Patent: Jul. 17, 2012

(54) PATIENT POSITIONING IMAGING DEVICE AND METHOD

(75) Inventors: Jean-Claude Amelia, Erquelinnes (BE); Frédéric Genin, Ottignies (BE)

(73) Assignee: Ion Beam Applications SA, Louvain-la-Neuve (BE)

( * ) Notice: Subject to any disclaimer, the term of this patent is extended or adjusted under 35 U.S.C. 154(b) by 715 days.

(21) Appl. No.: 11/721,112

(22) PCT Filed: Dec. 12, 2005

(86) PCT No.: PCT/BE2005/000183
§ 371 (c)(1),
(2), (4) Date: Aug. 21, 2009

(87) PCT Pub. No.: WO2006/060886
PCT Pub. Date: Jun. 15, 2006

(65) Prior Publication Data
US 2009/0304153 A1    Dec. 10, 2009

(30) Foreign Application Priority Data

Dec. 10, 2004  (EP) .................................. 04447273
Apr. 4, 2005   (EP) .................................. 05447076

(51) Int. Cl.
*A61N 5/10* (2006.01)
(52) U.S. Cl. ............. 378/65; 378/20; 378/196; 378/197
(58) Field of Classification Search .................... 378/11, 378/20, 65, 196, 197
See application file for complete search history.

(56) References Cited

U.S. PATENT DOCUMENTS

| | | | | |
|---|---|---|---|---|
| 5,329,567 A | * | 7/1994 | Ikebe ............................. | 378/20 |
| 5,537,452 A | * | 7/1996 | Shepherd et al. ............... | 378/65 |
| 5,751,781 A | * | 5/1998 | Brown et al. .................... | 378/65 |
| 5,851,182 A | * | 12/1998 | Sahadevan ...................... | 378/65 |
| 6,200,024 B1 | * | 3/2001 | Negrelli ......................... | 378/197 |
| 6,203,196 B1 | | 3/2001 | Meyer et al. | |
| 6,269,143 B1 | * | 7/2001 | Tachibana ....................... | 378/65 |
| 6,318,892 B1 | * | 11/2001 | Suzuki et al. .................. | 378/197 |
| 6,325,537 B1 | * | 12/2001 | Watanabe ....................... | 378/197 |
| 6,412,978 B1 | * | 7/2002 | Watanabe et al. .............. | 378/197 |
| 6,435,714 B1 | * | 8/2002 | Bruder ........................... | 378/196 |
| 6,582,121 B2 | * | 6/2003 | Crain et al. .................... | 378/197 |
| 6,614,871 B1 | * | 9/2003 | Kobiki et al. ................... | 378/20 |
| 6,619,840 B2 | * | 9/2003 | Rasche et al. ................. | 378/197 |
| 6,842,502 B2 | * | 1/2005 | Jaffray et al. ................... | 378/65 |
| 6,888,919 B2 | * | 5/2005 | Graf ................................ | 378/65 |
| 6,914,959 B2 | * | 7/2005 | Bailey et al. .................... | 378/65 |

(Continued)

*Primary Examiner* — Allen C. Ho (74) *Attorney, Agent, or Firm* — Fitch, Even, Tabin & Flannery, LLP (57) ABSTRACT

The present invention is related to a patient positioning imaging device for positioning a patient in a hadron therapy device provided with a rotatable gantry (20). The patient positioning imaging device comprises a rotatable structure (10) provided with an extensible arm or foldable pivoting arm (12) arranged for connecting an imaging beam source (121) and an extensible structure or foldable pivoting structure (14) arranged for carrying an imaging beam receiver (141). The rotatable structure (10) is arranged for taking CBCT shots of the patient while the patient is located in an offset position with respect to an isocentre of the hadron therapy device, said offset position being in the direction of a rotational axis of the rotatable gantry (20). The rotatable structure (10) is arranged for being rotated while the rotatable gantry (20) remains fixed, and while the extensible or pivoting arm (12) and the extensible or pivoting structure (14) are in extended or unfolded position.

8 Claims, 7 Drawing Sheets

U.S. PATENT DOCUMENTS

| | | | |
|---|---|---|---|
| 7,173,265 B2 * | 2/2007 | Miller et al. | 250/492.3 |
| 7,199,382 B2 * | 4/2007 | Rigney et al. | 250/492.1 |
| 7,570,739 B2 * | 8/2009 | Bergfjord et al. | 378/65 |
| 7,603,164 B2 * | 10/2009 | Uematsu | 600/427 |
| 7,640,607 B2 * | 1/2010 | Guertin et al. | 5/601 |
| 7,657,304 B2 * | 2/2010 | Mansfield et al. | 600/427 |
| 2003/0007601 A1 | 1/2003 | Jaffray et al. | |
| 2004/0024300 A1 | 2/2004 | Graf | |

\* cited by examiner

PATIENT POSITIONING IMAGING DEVICE AND METHOD

FIELD OF THE INVENTION

The present invention is related to a patient positioning imaging apparatus and method for positioning a patient in a hadron therapy device.

STATE OF THE ART

When a malignant tumour has been discovered in a patient's body, the tumour first needs to be visualised for further examination. This can for example be performed with a (third generation) 3D computed tomography (CT) scanning system. With the information collected in this way a clinical treatment plan can be generated. Then the actual treatment with a therapeutic apparatus can start.

In a known hadron therapy apparatus, like e.g. used in proton therapy, the therapeutic radiation beam, accelerated by an accelerator such as a cyclotron, is guided to the therapy room where the patient is fixed to a therapy table such as a therapy couch. Prior to irradiation, the therapy table must be positioned accurately by means of a positioning system, such that the affected part of the patient's body is in alignment with the therapeutic radiation beam.

Often irradiation is performed from a variety of different angles. A gantry system is then used to rotate the radiation source. For hadron therapy, typically, the hadronic particle, e.g. a proton, a neutron, or an alpha particle or carbon ion, is emitted out of a nozzle towards a particular target region of the patient, e.g. a tumour to be treated. Tumour volumes are defined in relation to a specific reference point called the isocentre. The isocentre occurs at a point where the axis of the nozzle beam path intersects the gantry axis of rotation. The isocentre remains fixed throughout the treatment process.

It is required that the patient be accurately positioned with respect to therapy device, so that the beam only irradiates the target as designed in the treatment planning. Otherwise, the beam could damage healthy cells within the patient's body. So, the precision of the patient positioning before treatment is highly critical to a successful operation.

Typically, the patient undergoing the therapy receives periodic treatments wherein the target is irradiated repeatedly over the course of an extended period of time. Therefore, before each treatment session, a proper positioning of the patient is required.

As already mentioned, the process of identifying the precise location of the target volume immediately prior to a dose of therapeutic radiation is of key importance. To ensure that the patient is accurately positioned with respect to the isocentre of the therapy device, the position of the target is initially determined with respect to one or more monuments within the body of the patient. This operation is performed in an outside diagnostic imaging system, such as a PET-scanner. In standard patient positioning, the monuments are comprised of points on the bones structure of the patient and the location of the target is then determined with respect to these monuments. The patient is then located on the couch of a patient positioner in the therapy device. The patient positioner is moved to the so-called 'set-up position', where the patient position is determined through the use of radiographs, laser-lights and/or other localisation aids having the capability to locate said monuments. A correction is determined as required. The patient positioner is then used to move the patient to the successive treatment positions. In the set-up position, the patient is located at or near the isocentre. In this approach it is assumed that the tumour never moves between the time of the CT scan and all the treatment days.

This limitation is taken away by Cone Beam Computed Tomography (CBCT). A CBCT allows the therapist to reconstruct a 3D image of the inside of a patient body. On the image, one can see the bones structure, but also the soft tissues. It allows the therapist to align the patient by performing a 3D manual or automatic matching of any part of the patient body. It also helps the therapist in monitoring the differences between the CT scan before treatment and the tumour's evolution during the treatment period. Hadron therapy being today's most precise radiotherapy technique, it can take full advantage of a CBCT device to help the therapist in better positioning the patient.

Figure 1:
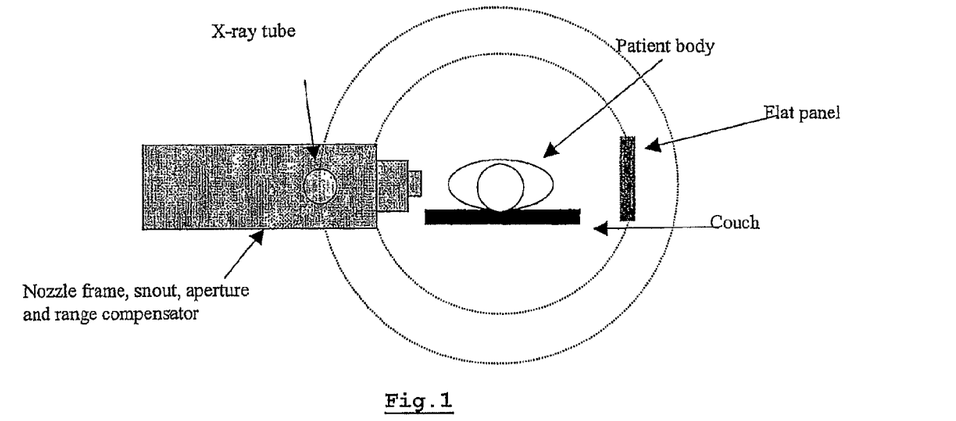
FIG. 1 represents a CBCT image acquisition system according to the state of the art.

One solution for obtaining CBCT images in a hadron therapy environment would be as shown in FIG. 1. The acquisition system of such a CBCT system is made of an X-ray tube located in the nozzle and a flat panel. The two devices are positioned on each side of the patient and turn around the patient in a possible—theoretically—full 360° rotation while the successive X-ray shots are taken. However, as compared to conventional radio-therapy, where the X-ray tube and the flat panel are placed on the gantry at 90° compared to the beam axis, in proton-therapy several different constraints have been identified in the configuration as in FIG. 1:

- to minimise the lateral penumbra, the aperture (and consequently the nozzle supporting the aperture) is brought as closely as possible to the patient. One only clears the distance to allow patient positioner movement and aperture/range compensator exchange. It forbids the movement of the x-ray tube or the flat panel between the nozzle and the patient couch.
- the X-ray tube inside the nozzle is too far away from the isocentre to allow having the same geometry (i.e. distances between X-ray tube, patient and flat panel) as in the conventional radio-therapy world. Because of the nozzle frame and the aperture support, the field of view using the X-ray tube inside the nozzle would be too small,
- full rotation of a heavy gantry structure for obtaining images is felt as unpractical.

An alternative possible solution would be to position a CBCT system in the treatment room, which clearly would use treatment room space and thus be an inconvenience for the therapists.

In patent document US2004/024300-A1 a method and apparatus for positioning a multiple-energy imager to oppose one or more radiation sources is disclosed. A therapeutic radiation source capable of propagating an electron beam in the MV energy range to generate high energy X-ray radiation and a diagnostic kV X-ray radiation source can be positioned on separate arms (gantries), where one arm is nestled within the other. The two arms have a common pivot axis and can pivot independently. In addition, the inner arm can extend and retract the diagnostic radiation source for positioning and clearance. In this document, in order to provide multiple X-ray views at different angles for generating 3-dimensional images of the target volume, it is necessary, for maintaining clearance between diagnostic radiation source and therapeutic radiation source, to rotate both arms (gantries) together.

In order to provide the required comfort to a patient it is desirable to obtain the images for patient positioning in a time as short as possible. One minute is regarded as an acceptable duration for taking the positioning images, and should not be exceeded.

AIMS OF THE INVENTION

The present invention aims to provide a patient positioning imaging device and method for positioning a patient in a hadron therapy device that allow to overcome several drawbacks of the prior art solutions.

SUMMARY OF THE INVENTION

The present invention relates to a patient positioning imaging device for positioning a patient in a hadron therapy device. The hadron therapy device is provided with a rotatable gantry. The patient positioning system comprises a rotatable structure provided with an extensible arm or a foldable pivoting arm arranged for connecting an imaging beam source and an extensible structure or a foldable pivoting structure arranged for carrying an imaging beam receiver. The rotatable structure is arranged for taking CBCT shots of the patient while the patient is located in an offset position (in the direction of a rotational axis of the rotatable gantry) with respect to an isocentre of the hadron therapy device, whereby the rotatable structure is arranged for being rotated while the rotatable gantry remains fixed, and while the extensible or pivoting arm and extensible or pivoting structure are in their extended or unfolded position.

In a preferred embodiment the imaging beam source comprises an imaging X-ray radiation source. Preferably the imaging beam receiver is a flat image panel. Advantageously, the pivoting arm is further provided with a hole allowing an X-ray beam to pass through the pivoting arm when the pivoting arm is in retracted or folded position.

In an advantageous embodiment the pivoting arm and the pivoting structure have a different length. This allows smoothly folding the positioning device.

In a further embodiment the rotatable structure further comprises at least one recess.

In a specific embodiment the rotatable gantry and the rotatable structure have a same rotational axis.

Most advantageously the rotatable structure is typically mounted on the rear of the rotatable gantry. Optionally it can be mounted on the rear via an extensible support arm.

In an advantageous embodiment the patient positioning imaging device further comprises a telescopic structure on which a flat panel is mounted, said structure being shiftable over said recess.

In another object the invention relates to a method for determining patient positioning information to be used in hadron beam therapy as previously described. It comprises the steps of:
   putting a patient on a couch near treatment position,
   unfolding the pivoting structure and the pivoting or the extensible arm of a patient positioning imaging device as previously described,
   using a patient positioner for positioning the couch in an offset position in the direction of a rotational axis of the rotatable gantry,
   triggering the rotation of the rotatable structure for obtaining a sequence of CBCT shots,
   calculating a 3D image of the patient based on the sequence of CBCT shots,
   comparing the 3D image to an image coming from a treatment planning system to compute a correction vector for the patient positioner,
   moving the patient positioner to a corrected treatment position based on said correction vector.

In a further object the invention relates to a method for determining information on a patient's position or respiratory cycle phase, said information to be used in hadron beam therapy. The method comprises the steps of:
   putting a patient on a couch near treatment position,
   unfolding said pivoting structure and said pivoting arm or extending said extending structure and extending arm of a patient positioning imaging device as previously described,
   extending the extensible support arm to bring the patient positioning imaging device at an isocentre of said hadron therapy device,
   imaging the patient using radiography or fluoroscopy in order to determine said information on the patient's position or on the respiration cycle of the patient.

DETAILED DESCRIPTION OF THE INVENTION

The present invention discloses a patient positioning imaging device and method for positioning a patient in a hadron therapy device. To overcome the above-mentioned constraints, the solution according to the present invention consists in providing a patient positioning imaging system comprising a small and light rotatable structure inside the gantry of the beam therapy device. This offers several advantages:
   it allows to have enough space to install the X-ray tube and the flat panel at the same distance as in conventional radiotherapy (RT).
   it allows to have the full field of view as in conventional RT,
   it allows to have a system fully independent from the orthogonal flat panels. There is no need to rotate anything when taking orthogonal shots.
   no treatment room space is used so that it remains fully available for the therapists.
   the room for the gantry rolling floor remains available and there is no need to move the floor during the rotation of the CBCT light structure,
   it is not required to rotate the gantry while taking the X-ray shots.

Figure 2:
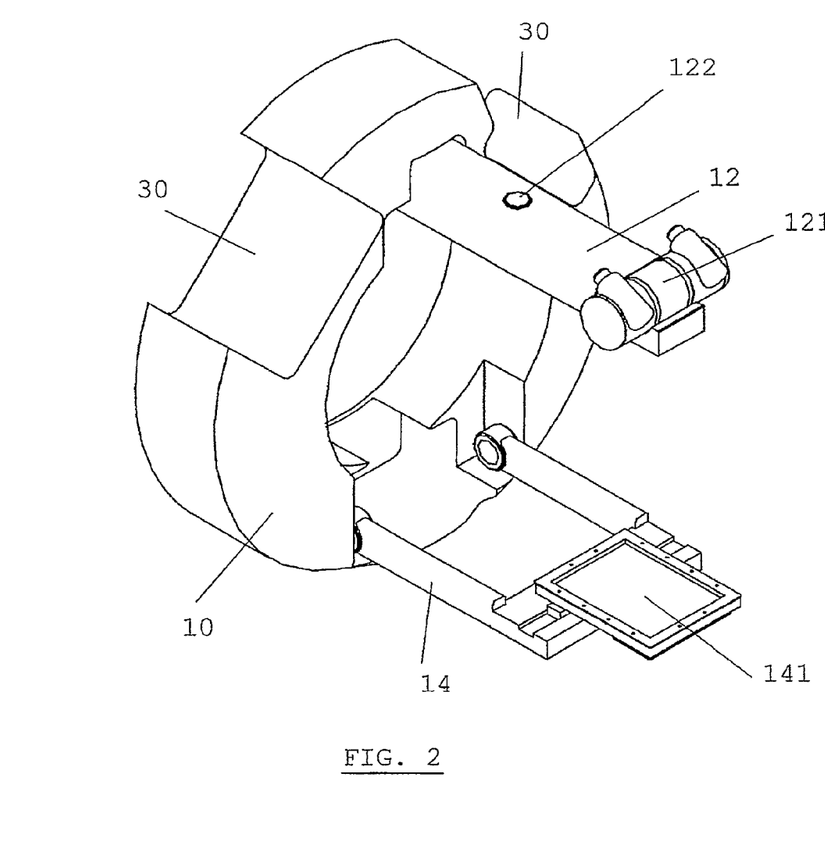
FIG. 2 represents a patient positioning imaging device according to the invention with unfolded movable arms.
Figure 3:
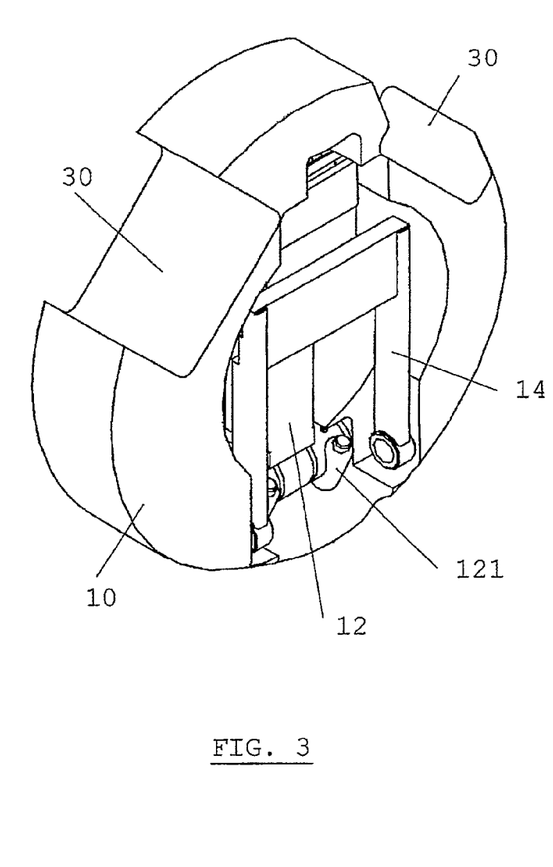
FIG. 3 represents a patient positioning imaging device according to the invention with folded movable arms.

The patient positioning imaging device as shown in FIGS. 2 and 3 comprises a light rotatable structure 10 provided with a pivoting arm 12 to which imaging beam source 121 can be connected and a pivoting structure 14 or a retracting structure arranged for carrying a imaging beam receiver 141. Typically the imaging beam source 121 comprises an imaging X-ray radiation source as shown in FIG. 2.

The geometry of the device further allows to keep the centre of the CBCT structure empty in view of a possible installation of an imaging X-ray radiation source located behind the structure 10 and directed along the gantry rotation axis. A hole 122 is foreseen for allowing this X-ray beam to pass through the rotating structure or the pivoting arm 12 when folded.

Because the pivoting arm 12 and the pivoting structure 14 have a different length, they can smoothly be folded as show in FIG. 3. Other means for retracting the pivoting arm 12 and the pivoting structure 14 can however be envisaged, such as arms holding side by side.

FIGS. 2 and 3 further also show two recesses 30, allowing a telescopic structure, on which a flat panel is mounted, to pass.

In a typical embodiment the rotatable structure is mounted in the rear of the rotatable gantry of a hadron therapy device. The rotatable gantry and the rotatable structure advantageously have a same rotational axis.

Figure 4A:
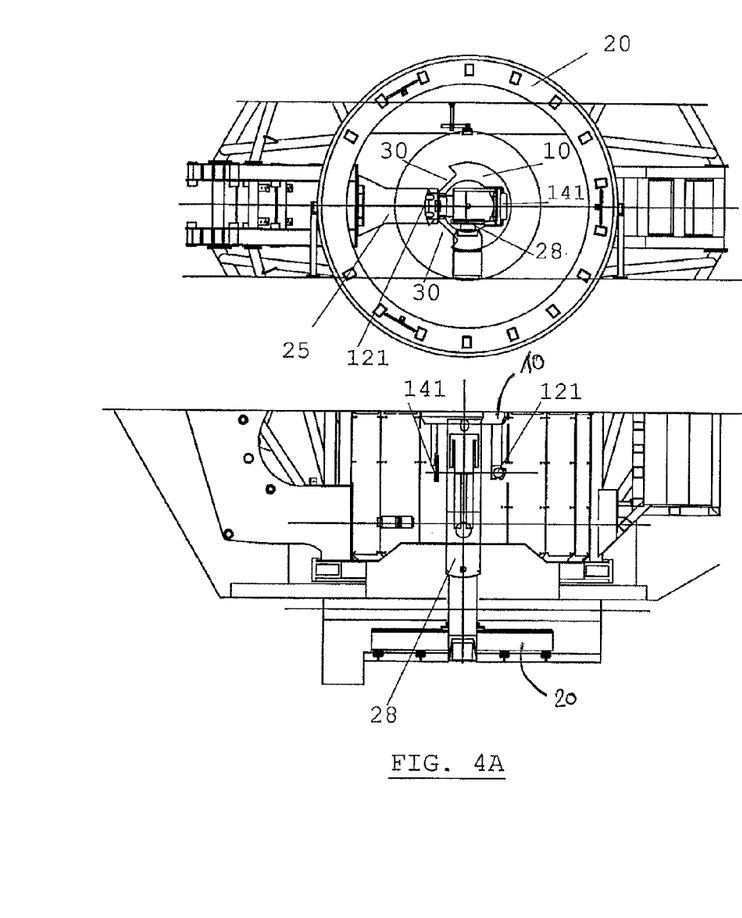
FIG. 4A represents a front view and a top view of a therapeutic apparatus comprising an unfolded patient positioning imaging device according to the invention and a patient in CBCT set-up position (offset position).
Figure 4B:
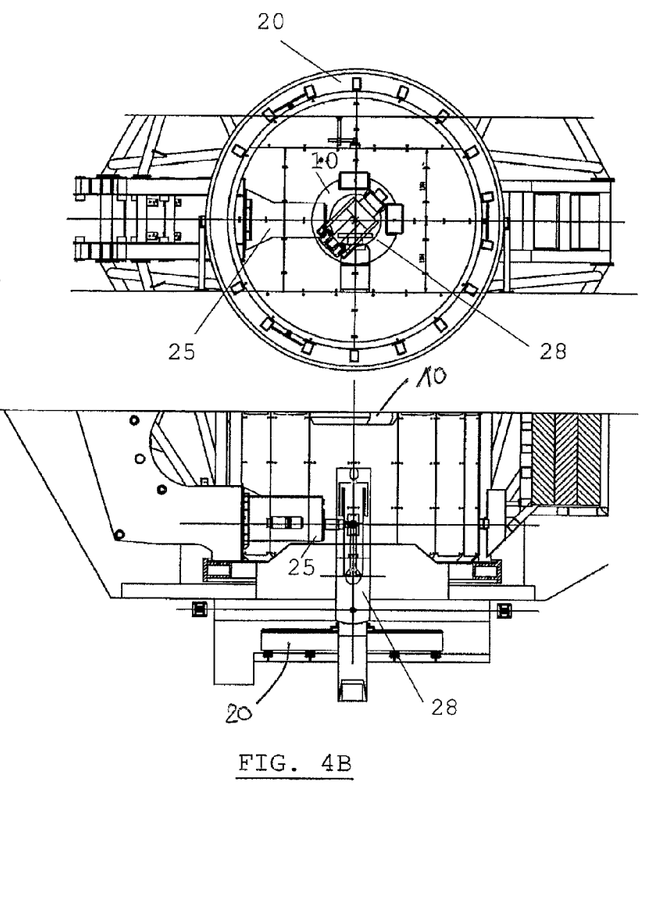
FIG. 4B represents a front view and a top view of a therapeutic apparatus comprising a folded patient positioning imaging device according to the invention and a patient in treatment position.

FIGS. 4A and 4B show the patient positioning imaging device mounted onto the gantry of a hadron therapy device. They each give a front view (wherein the rotatable structure is in the rear) and a top view (through the gantry of the hadron therapy device). FIG. 4A shows the rotatable structure in an unfolded state and FIG. 4B in a folded, resting position. The image beam receiver 141 is folded above the X-ray tube structure 121. FIG. 4A shows the patient lying on couch 28 when a patient positioner (i.e. a mechanical device allowing movements of the couch along three translational and three rotational degrees of freedom) has moved the patient to the rear of the gantry 20 in the so-called 'CBCT set-up position'. The patient positioning imaging device is unfolded and imaging beam source 121 and flat panel imager 141 are used for obtaining a CBCT image. In FIG. 4B, where the pivoting arm 12 and pivoting structure 14 are in a folded state, the patient is placed in the set-up position or the treatment position and is irradiated with a therapeutic beam from nozzle 25. One notes there is an offset between the CBCT set-up position (FIG. 4A), which is the position where the CBCT images are obtained, and the treatment position of FIG. 4B. Note also that the lowest point of the positioning imaging device when mounted on the rear of the gantry 20 is still above the floor level. This allows a full rotation of the rotatable structure 10, while leaving the gantry floor in place.

In a specific embodiment the flat panel imager has a landscape orientation, an active area of 39.7×29.8 cm$^2$ with 194 micron pixel pitch, and a pixel count of 2048×1536 pixels. It can operate at a frame rate of 7.5 fps in full resolution mode and at a frame rate of 30 fps in 2×2 binned mode, where the pixel count is reduced to 1024×768 pixels$^2$.

For example, the flat panel imager may be an amorphous silicon (a-Si) imager available from Varian Medical Systems of Palo Alto, Calif., under the trade name PaxScan 4030A. The PaxScan 4030A detectors are each 40 cm×30 cm. The detectors may be coupled to signal processing circuitry comprising a preamplifier stage with dynamically controllable signal gain, as described in US patent US-6486808, to improve contrast resolution and dynamic range.

The solution of the invention also lends itself to be integrated in a therapeutic apparatus provided with a so-called gantry rolling floor, i.e. a floor staying in horizontal position while the gantry rotates.

Figure 5A:
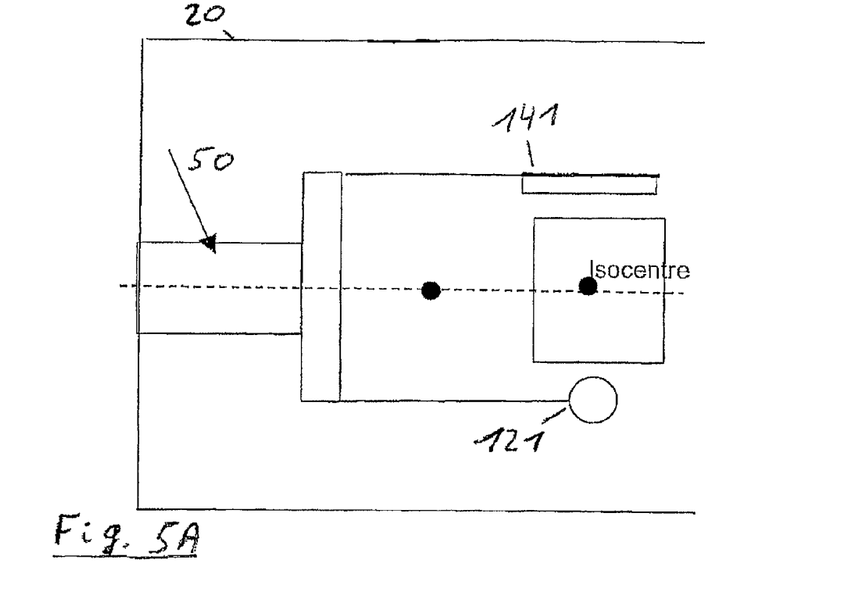
FIG. 5 represents an embodiment wherein the rotatable structure is mounted on an extensible support arm.
Figure 5B:
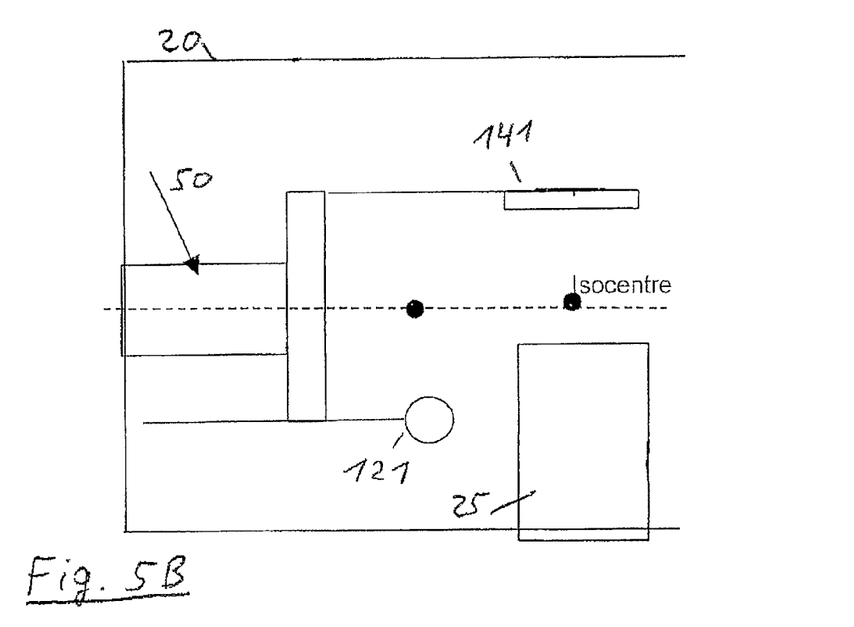

FIG. 5 represents a specific embodiment where the rotatable structure 10 is mounted on an extensible support arm 50. The extensible support arm 50 allows several additional positions. As shown in FIG. 5A, it allows the imaging beam source 121 and the imaging beam receiver 141 to be used in a non-offset position, i.e. in the isocentre. The imaging beam receiver and the imaging beam source can be used in the isocentre in two different modalities:

without rotation of the rotatable structure. The imaging system can be used to acquire a still radiograph of the patient, for example to check the patient position based on bony landmarks. Alternatively, the imaging system can be used for fluoroscopy. In fluoroscopy a sequence of radiographs is acquired in order to monitor the motion of the patient, for example to monitor the respiration cycle of the patient.

with rotation of the rotatable structure. The imaging receiver and the imaging beam source are rotated around the patient to acquire a series of projections. Contrarily to Cone Beam Computed Tomagraphy, it is not possible to rotate at 360° around the patient, due to the geometrical clash with the nozzle. Only a partial set of projection along an arc of circle can be recorded. An algorithm can be used to reconstruct the 3D structure of the patient from this incomplete data set, for example using digital tomosynthesis.

Alternatively (see FIG. 5B), only the extensible or pivoting arm 12 can be retracted. In this case the imaging beam receiver can be used in combination with the X-ray tube in the nozzle.

Figure 6A:
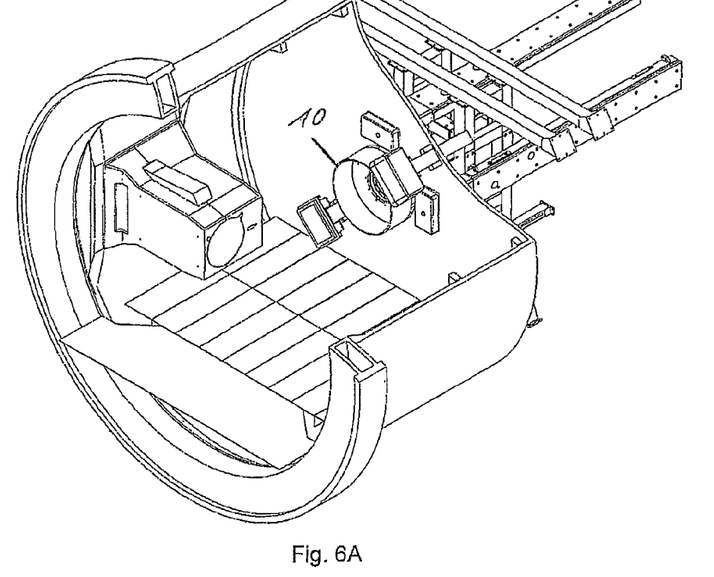
FIG. 6 represents an embodiment with an extensible arm and an extensible structure.
Figure 6B:
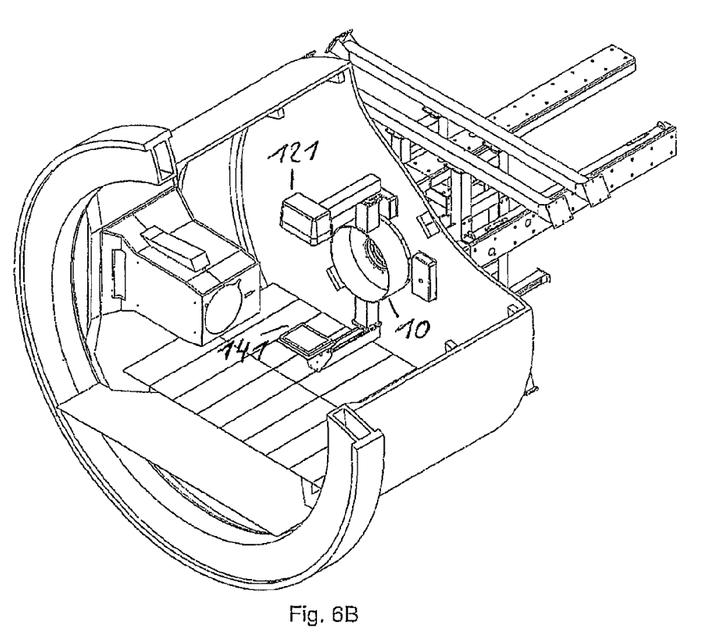
Figure 6C:
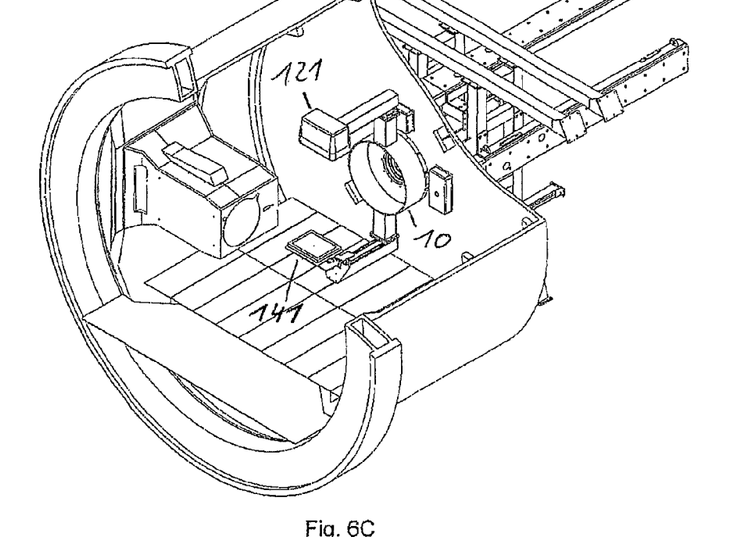
Figure 6D:
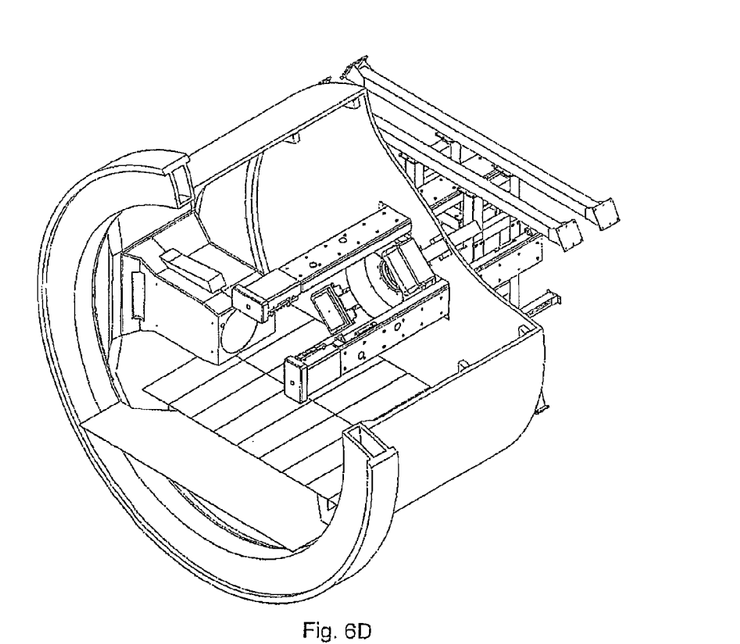
Figure 6E:
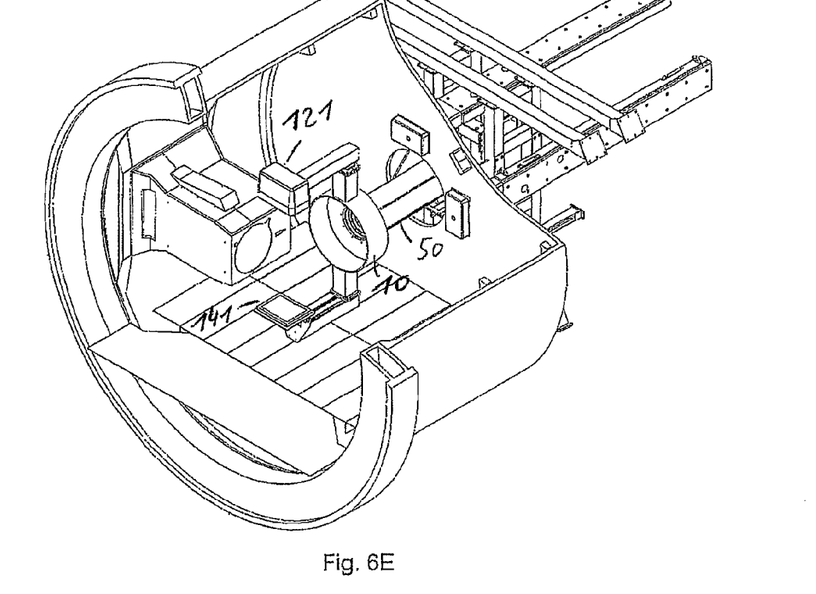
Figure 6F:
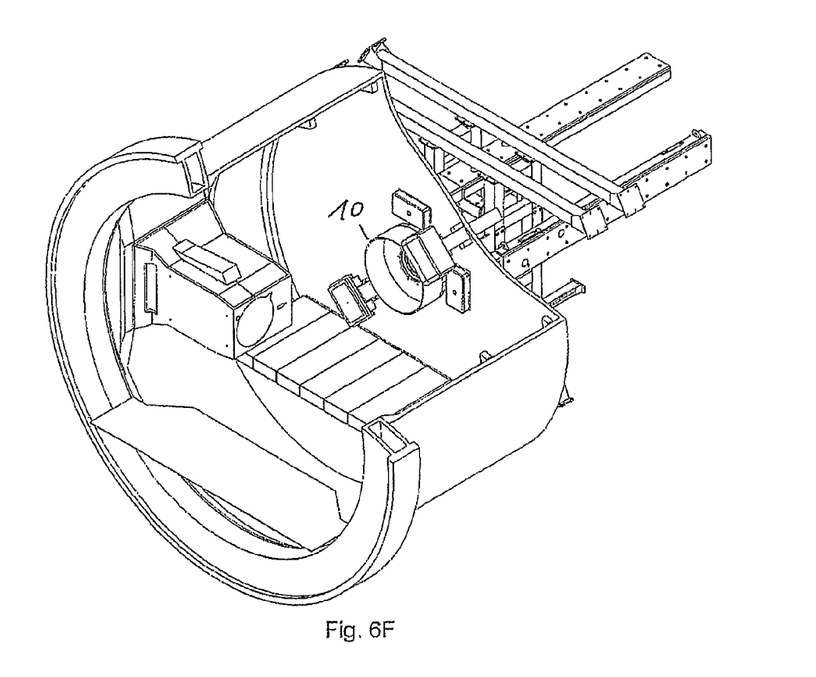

In another preferred embodiment the patient positioning imaging system can have an arm that can be extended and retracted instead of a foldable pivoting arm. Equally the foldable pivoting structure can be replaced by an extensible structure. FIG. 6A shows a rotatable structure 10 in a retracted position. FIG. 6B shows the rotatable structure 10 in the extended position. Both the imaging beam receiver 141 and the imaging beam source 121 are extended. The rotatable structure has rotated counterclockwise over 45° with respect to the position shown in FIG. 6A. FIG. 6C shows the rotatable structure in the extended position. In addition to FIG. 6B, the imaging beam receiver 141 has been shifted in a direction perpendicular to the plane defined by the rotational axis of the rotatable structure and the imaging beam source in order to provide an increased imaging volume. FIG. 6D shows an important advantage offered by the present invention. It shows that with the rotatable structure in the retracted position, another imaging structure providing alternative imaging technologies can be extended. In other words, FIG. 6D illustrates the rotatable structure 10 is compatible with the use of other imaging technologies. In FIG. 6E the rotatable structure is again extended. The extensible support arm 50 is also in extended position. This allows using the imaging beam receiver on the extensible structure and the imaging beam source on the extensible arm in the non-offset position, as previously explained. Finally, FIG. 6F shows the rotatable structure in the retracted position together with a rolling floor also in the retracted position.

The invention also relates to a method for determining patient positioning information prior to starting a hadron therapy session.

First the concept of 'CBCT setup position' needs to be specified. The aim of the position is exactly the same as the conventional 'setup position'. The only difference between those two positions is a given offset in the gantry axis direction. A typical distance is in the range of 850 to 1000 mm, which is obtainable with current patient positioning devices.

Once the correction in position (using the CBCT) is computed, the therapist will use the patient positioning device for making the required translation and isocentric rotations plus an opposite given offset in the gantry axis direction. The method comprises the steps of:

1. Placing the patient on the couch near treatment position,
2. Unfolding the pivoting arm 12 and pivoting structure 14 of the patient positioning imaging device as above described,
3. Using the patient positioner for positioning the couch in an offset position in the direction of a rotational axis of the rotatable gantry, 4. Triggering the rotation of the rotatable structure (10) of the patient positioning imaging device, yielding a sequence of CBCT shots,
5. Calculating a 3D image of the patient,
6. Comparing the 3D image to an image coming from a treatment planning system (TPS) (manually or automatically) to compute a correction vector for the patient positioner,
7. Moving the patient positioner to a corrected position based on said correction vector.

Note that at any point in time:
before going to 'CBCT setup position' (i.e. offset position)
between the 'CBCT setup position' and the treatment position
once the patient is in treatment position and before treatment,
the therapist can always take one or more orthogonal X-ray shots and compare them to the corresponding DRR so that he can check his alignment process and take actions if needed.

The embodiment wherein the rotatable structure 10 is mounted on an extensible support arm 50 can advantageously be used in a method for determining the patient position or for determining the phase of the respiratory cycle of the patient to be used in hadron beam therapy. Such method comprises the step of:
putting a patient on a couch 28 near treatment position,
unfolding said pivoting structure and said pivoting arm or extending said extending structure and extending arm of a patient positioning imaging device as described,
extending the extensible support arm 50 to bring the patient positioning imaging device at isocentre,
imaging the patient using radiography or fluoroscopy in order to determine information on the position of the patient or on the respiration cycle of the patient.

Using the design and method of the invention, it is possible to obtain a sequence of CBCT shots at different angles, by rotating the rotatable structure (10), while maintaining the rotatable gantry (20) in a fixed position. A rotatable gantry (20) used in a hadron therapy device is a heavy device, and cannot easily be moved in the time span allocated for taking the images.

The invention claimed is:

1. A hadron therapy device comprising:
a rotatable gantry and a patient positioning imaging device configured to position a patient, said patient positioning imaging device comprising an imaging beam source, an imaging beam receiver, and a rotatable structure provided with an extensible arm or a foldable pivot arm configured to connect said imaging beam source and an extensible structure or a foldable pivoting structure configured to carry said imaging beam receiver, whereby said rotatable structure is configured to take CBCT shots of said patient while said patient is located in an offset position with respect to an isocentre of said hadron therapy device, said offset position being in the direction of a rotational axis of said rotatable gantry, whereby said rotatable structure is configured to be rotated while said rotatable gantry remains fixed, and while said extensible or foldable pivoting arm and said extensible or foldable pivoting structure are in extended or unfolded position, wherein said rotatable structure is mounted on the rear of said rotatable gantry.

2. The hadron therapy device as in claim 1, wherein said imaging beam source comprises an imaging x-ray radiation source.

3. The hadron therapy device as in claim 1, wherein said imaging beam receiver is a flat image panel.

4. The hadron therapy device as in claim 1, wherein said rotatable structure further comprises at least one recess.

5. The hadron therapy device as in claim 1, wherein said rotatable structure and said rotatable gantry of said hadron therapy device have a same rotational axis.

6. The hadron therapy device as in claim 1, wherein said rotatable structure is mounted on the rear of said rotatable gantry via an extensible support arm.

7. A method for determining patient positioning information to be used in hadron therapy, comprising the steps of:
putting a patient on a couch near treatment position in a hadron therapy device comprising a rotatable gantry and a patient positioning imaging device configured to position a patient, said patient positioning imaging device comprising an imaging beam source, an imaging beam receiver, and a rotatable structure provided with an extensible arm or a foldable pivoting arm configured to connect said imaging beam source and an extensible structure or a foldable pivoting structure configured to carry said imaging beam receiver, whereby said rotatable structure is configured to take CBCT shots of said patient while said patient is located in an offset position with respect to an isocentre of said hadron therapy device, said offset position being in the direction of a rotational axis of said rotatable gantry, whereby said rotatable structure is configured to be rotated while said rotatable gantry remains fixed, and while said extensible or foldable pivoting arm and said extensible or foldable pivoting structure are in extended or unfolded position;
unfolding said foldable pivoting structure and said foldable pivoting arm or extending said extensible structure and said extensible arm of said patient positioning imaging device comprised in said hadron therapy device;
using a patient positioner for positioning said couch in an offset position in the direction of said rotational axis of said rotatable gantry;
triggering the rotation of the rotatable structure for obtaining a sequence of CBCT shots;
calculating a 3D image of the patient based on said sequence of CBCT shots;
comparing the 3D image to an image coming from a treatment planning system to compute a correction vector for said patient positioner; and
moving said patient positioned to a corrected treatment position based on said correction vector.

8. A method for determining information on patient's position or respiratory cycle phase, said information to be used in hadron therapy, comprising the steps of:
putting a patient on a couch near treatment position;
unfolding said foldable pivoting structure and said foldable pivoting arm or extending said extensible structure and said extensible arm of a patient positioning imaging device comprised in a hadron therapy device as in claim 6;
extending the extensible support arm to bring the patient positioning imaging device to said isocentre of said hadron therapy device; and
imaging the patient using radiography or fluoroscopy in order to determine said information on the patient's position or on the respiratory cycle of the patient.

* * * * *